(12) United States Patent
Sekiguchi et al.

(10) Patent No.: US 9,961,280 B2
(45) Date of Patent: May 1, 2018

(54) IMAGE FORMING APPARATUS AND IMAGING SYSTEM

(71) Applicant: CANON KABUSHIKI KAISHA, Tokyo (JP)

(72) Inventors: Ryota Sekiguchi, Hiratsuka (JP); Toshihiko Ouchi, Machida (JP)

(73) Assignee: CANON KABUSHIKI KAISHA, Tokyo (JP)

(*) Notice: Subject to any disclaimer, the term of this patent is extended or adjusted under 35 U.S.C. 154(b) by 102 days.

(21) Appl. No.: 14/763,548

(22) PCT Filed: Feb. 25, 2014

(86) PCT No.: PCT/JP2014/055200
§ 371 (c)(1),
(2) Date: Jul. 27, 2015

(87) PCT Pub. No.: WO2014/136698
PCT Pub. Date: Sep. 12, 2014

(65) Prior Publication Data
US 2015/0365611 A1    Dec. 17, 2015

(30) Foreign Application Priority Data
Mar. 8, 2013    (JP) .................................. 2013-046193

(51) Int. Cl.
*H04N 5/357*    (2011.01)
*G01S 17/89*    (2006.01)
(Continued)

(52) U.S. Cl.
CPC ......... *H04N 5/357* (2013.01); *G01N 21/3581* (2013.01); *G01N 22/02* (2013.01);
(Continued)

(58) Field of Classification Search
CPC ........................... H04N 5/357; H04N 5/3745; H01L 27/14609; G01N 21/3581; G01S 17/89; G01S 7/4914
See application file for complete search history.

(56) References Cited

U.S. PATENT DOCUMENTS 5,856,667 A    1/1999    Spirig et al.
6,519,076 B2   2/2003    Fisher et al.
(Continued)

FOREIGN PATENT DOCUMENTS

JP    09-197042    7/1997
JP    10-508736    8/1998
(Continued)

OTHER PUBLICATIONS

Japanese Office Action dated Dec. 6, 2016 during prosecution of related Japanese application No. 2013-046193.

*Primary Examiner* — Tony Ko
(74) *Attorney, Agent, or Firm* — Fitzpatrick, Cella, Harper & Scinto

(57) ABSTRACT

Provided by the present invention is an image forming apparatus wherein a signal to noise ratio is improved without reducing a video rate of a real-time moving image. The image forming apparatus comprises:
a pixel 101 having an electromagnetic wave detecting element 111 configured to detect an electromagnetic wave;
a switch 110 configured to read out a signal from the pixel;
a signal generating unit 102 configured to generate a signal 114 having a predetermined period, wherein the pixel is connected to a transmission line 103 for supplying, to the pixel, the signal having the predetermined period, and to a scanning line 106 and 107 for reading out the signal from the pixel through the switch, and
(Continued)

the pixel has a frequency converting element 113 configured to convert a frequency of a detection signal of the electromagnetic wave detecting element, using the signal having the predetermined period.

17 Claims, 8 Drawing Sheets

(51) Int. Cl.
*G01S 7/491* (2006.01)
*G01N 22/02* (2006.01)
*G01N 21/3581* (2014.01)
*H01L 27/146* (2006.01)
*H04N 5/3745* (2011.01)

(52) U.S. Cl.
CPC ............ *G01S 7/4914* (2013.01); *G01S 17/89* (2013.01); *H01L 27/14609* (2013.01); *H01L 27/14643* (2013.01); *H04N 5/3745* (2013.01)

(56) References Cited

U.S. PATENT DOCUMENTS

| | | | |
|---|---|---|---|
| 6,559,798 B1 | 5/2003 | Marumoto | |
| 6,812,447 B2 | 11/2004 | Tanaka | |
| 7,119,350 B2 | 10/2006 | Hashimoto | |
| 9,040,922 B2* | 5/2015 | Gomez Rivas | G01J 3/02 |
| | | | 250/341.1 |
| 9,164,042 B2 | 10/2015 | Aiko | |
| 9,488,573 B2* | 11/2016 | Edwards | A61B 5/0048 |
| 2002/0067480 A1 | 6/2002 | Takahashi | |
| 2004/0155192 A1 | 8/2004 | Tran et al. | |

FOREIGN PATENT DOCUMENTS

| | | |
|---|---|---|
| JP | 2000-196334 | 7/2000 |
| JP | 2001-272334 | 10/2001 |
| JP | 2002-51357 | 2/2002 |
| JP | 2004-32682 | 1/2004 |
| WO | 2001/66030 | 9/2001 |
| WO | 2012/108306 | 8/2012 |

\* cited by examiner

IMAGE FORMING APPARATUS AND IMAGING SYSTEM

This application is a national phase of PCT Application No. PCT/JP2014/055200 filed Feb. 25, 2014, which in turn claims benefit of Japanese Application No. 2013-046193 filed Mar. 8, 2013.

TECHNICAL FIELD

The invention relates to an image forming apparatus, an imaging system, and the like and, more particularly, to, for example, a 2-dimensional array detecting element, an image forming apparatus of a synchronous detection type using such an element, and an imaging system.

BACKGROUND ART

In recent years, a development of such an image forming apparatus that an electromagnetic wave containing a frequency component of at least a part of a frequency area in a range from a millimeter wave band to a terahertz band (from 30 GHz to 30 THz) is detected and an intensity of each of pixels which are two-dimensionally arranged can be imaged has been started. Such an electromagnetic wave is also simply called "terahertz wave" or he like hereinbelow. Such a development has been started because the terahertz wave has the following nature and is considered to be useful in industries. First, the terahertz wave passes through a non-metallic substance in a manner similar to X-rays. Second, a number of absorption spectra which are peculiar to a biological molecule, medical and pharmaceutical products, or the like exist in such a frequency band. Third, the terahertz wave has space resolution necessary to many imaging uses. From the above feature, as application fields of the terahertz wave, a spectral analysis technique in the substance, a safe fluoroscopic imaging apparatus in place of the X-rays, an analysis technique of a biological molecule or medical and pharmaceutical products, and the like are considered.

As for the detecting element constructing the image forming apparatus in such a frequency area, hitherto, there are many detecting elements using a thermal detection. They are called "direct detection" or "video detection" and are a detecting method which is liable to be influenced by a low frequency noise such as a 1/f-noise or the like in the element. As a detecting method of the electromagnetic wave, a method called a synchronous detection different from the direct detection is known. The synchronous detection is a method whereby the electromagnetic wave to be detected is modulated with respect to time by a RF or the like and the modulation signal detected by the detecting element is demodulated by using a reference signal synchronized with the RF, is returned to a detection signal, and is detected. Generally, such a method is difficult to be influenced by the low frequency noise in the electromagnetic wave detecting element. In recent years, a method other than the thermal detection in the frequency area in the range from the millimeter wave band to the terahertz band has also been developed. Therefore, if such a nature of the synchronous detection is used, there is a possibility that a 2-dimensional array detecting element which can perform image forming and image pickup operations with a low noise and at a high sensitivity is realized.

PTL 1 discloses a method of lastly demodulating modulation signals of all pixels in a lump in an image forming sensor apparatus in a light area. Such a method is very convenient because it can use a commercially available image pickup apparatus as it is. Even suitable conditions are settled, an image can be photographed at a high sensitivity as a real-time moving image as if an ordinary television program was seen. PTL 2 likewise discloses an image forming sensor apparatus in a light area, wherein memory cells are arranged in a pixel and the synchronous detection is performed. Such a restriction of a CCD (Charge Coupled Device) that a signal has to be completely read out of the pixel during the photographing can be avoided. PTL 3 discloses a heterodyne detecting apparatus for forming an image in a millimeter wave band, wherein a weak electromagnetic wave generated from an object can be photographed.

CITATION LIST

Patent Literature

PTL 1: Japanese Patent Application Laid-Open No. 2001-272334
PTL 2: Japanese Patent Application Laid-Open No. H10-508736
PTL 3: Japanese Patent Application Laid-Open No. H09-197042

SUMMARY OF INVENTION

Technical Problem

However, in the related art disclosed in PTL 1, if it is intended to assure a video rate of the real-time moving image, a high frequency (for example, 200 MHz) has to be selected as a modulation frequency. Thus, a high frequency wiring, a switch for a high frequency, or a filter (including an amplifier) are necessary to process the signal obtained after the image pickup. The larger the number of pixels is (multi-pixel), the higher modulation frequency is required. In the related art disclosed in PTL 2, since the discrete signal which was integrated with respect to the time by using the memory cells is handled, the real-time moving image is not an object. In the related art disclosed in PTL 3, high frequency wirings, switches for the high frequency, or filters (including amplifiers) of the number as many as the number of pixels are necessary in order to read out the intermediate frequency signal in the millimeter wave heterodyne detection.

Solution to Problem

The invention is made in consideration of the foregoing problems and it is an object of the invention to provide a technique for improving a signal to noise ratio (=S/N ratio) of an image forming apparatus without reducing a video rate of a real-time moving image and without using high frequency parts.

According to an aspect of the present invention, an image forming apparatus comprises: a pixel having an electromagnetic wave detecting element configured to detect an electromagnetic wave; a switch configured to read out a signal from the pixel; a signal generating unit configured to generate a signal having a predetermined period, wherein the pixel is connected to a transmission line for supplying, to the pixel, the signal having the predetermined period, and to a scanning line for reading out the signal from the pixel through the switch, and the pixel has a frequency converting element configured to convert a frequency of a detection signal of the electromagnetic wave detecting element, using the signal having the predetermined period.

Further features of the present invention will become apparent from the following description of exemplary embodiments with reference to the attached drawings.

DESCRIPTION OF EMBODIMENTS

The invention relates to a construction for actively imaging an object to which an electromagnetic wave such as a terahertz wave or the like modulated to, for example, a few kHz to hundreds of MHz or the like has been irradiated. An image forming apparatus serving as an imaging unit constructed on the basis of such a construction, an imaging system including the image forming apparatus and an irradiating apparatus for performing an active illumination, and the like are disclosed in embodiments.

Embodiments and Examples of the invention will be described hereinbelow by using the drawings.

Embodiment 1

Figure 1A:
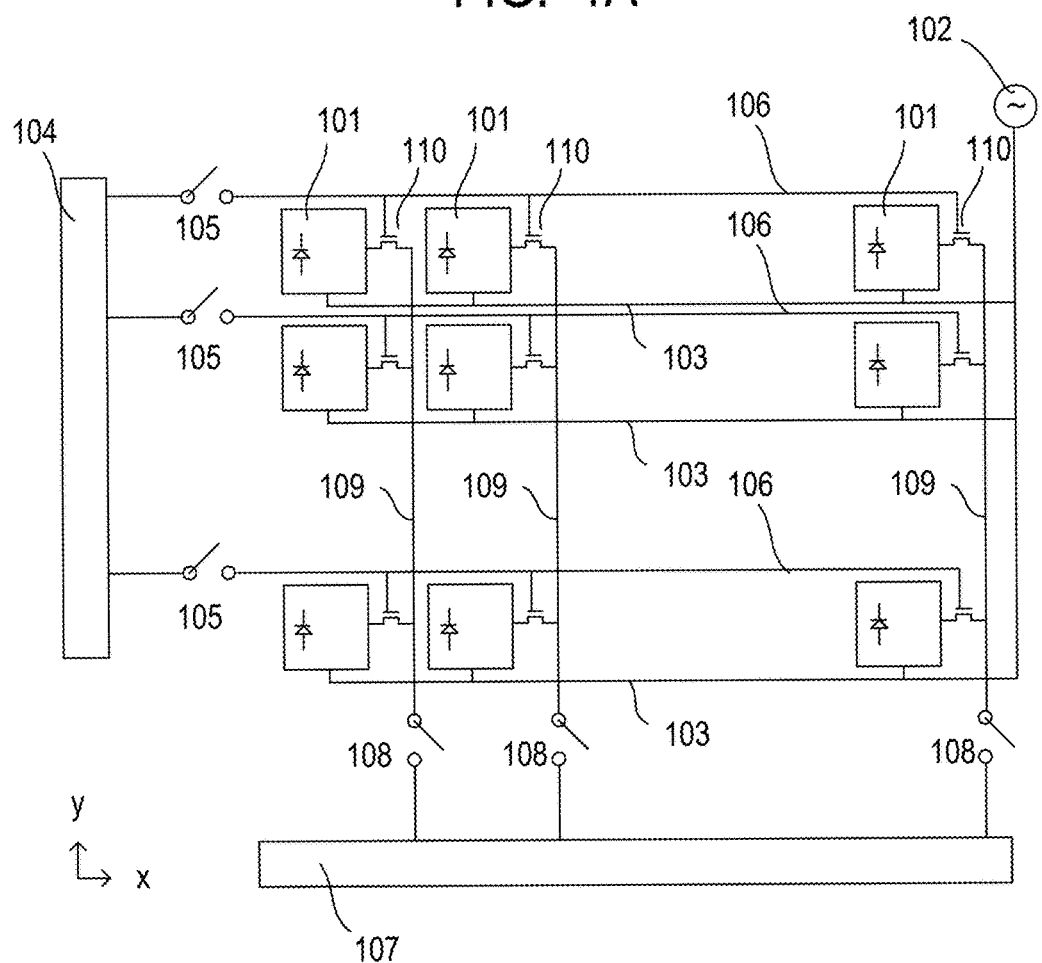
FIGS. 1A and 1B are diagrams illustrating a construction of an image forming apparatus according to an embodiment 1 of the invention.

An image forming apparatus according to an embodiment 1 will be described by using FIGS. 1A and 1B. FIG. 1A is a schematic diagram illustrating an array of pixels of the embodiment. A read-out line (scanning line for reading out a signal from the pixel through a switch) and a sine wave transmission line (transmission line for supplying the signal having a predetermined period to the pixel) are guided to each pixel. A pixel 101 has an electromagnetic wave detecting element for detecting an electromagnetic wave from an object. A plurality of pixels having a similar structure are two-dimensionally arranged. Such an array is not limited to two dimensions but may be one dimension. A sine wave generating unit 102 serving as a signal generating unit generates a signal having a predetermined period. A sine wave transmission line 103 is provided. In the embodiment, a frequency in a range from a few kHz to hundreds of MHz is selected. For example, such a range is a range from 10 kHz to 100 MHz. A y address circuit 104 and a y read-out line switch 105 are provided. The y address circuit 104 operates the y read-out line switch 105 in a read-out line 106 to be addressed. Similarly, an x address circuit 107 operates an x read-out line switch 108 in a read-out line 109 to be addressed. A transistor 110 is connected to each pixel 101 and functions as a selecting switch for reading out a signal current/charges in the pixel 101. A read-out circuit (not shown) of a detection signal which is successively sent from each pixel may be built in each of the x address circuit 107 and the y address circuit 104.

Figure 1B:
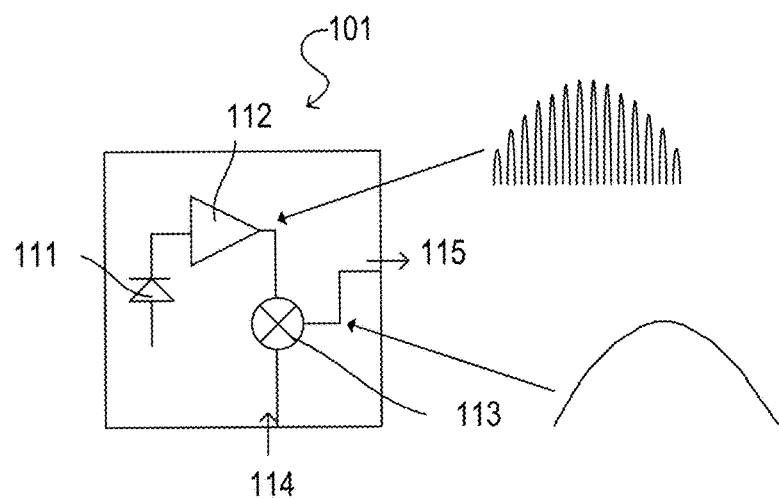

FIG. 1B is a schematic diagram illustrating one pixel of the embodiment. The pixel is constructed by: an electromagnetic wave detecting element 111; an amplifier 112 for amplifying the detection signal; a frequency converter 113 serving as a frequency converting element for frequency-converting an output of the electromagnetic wave detecting element by using the signal having the predetermined period; and the like. The detection signal from the detecting element 111 is mixed to a sine wave signal 114 guided to the pixel and becomes a demodulated analog signal 115. A detection signal from the object has been modulated by, for example, 1 MHz (sine-wave-like time waveform in FIG. 1B) and the sine wave signal 114 of 1 MHz is mixed to such a detection signal. If the frequency converter 113 such as a mixer or the like is used, the demodulated signal theoretically becomes 0 Hz (envelope of the sine-wave-like time waveform in FIG. 1B) like (1-1) MHz=0 Hz=DC (direct current). This is equivalent to a homodyne detection in the communication technique. Therefore, the well-known technique and well-known element in the communication technique can be also applied and integrated with the pixel 101. Or, if the sine wave signal 114 of 0.99 MHz is mixed, the frequency can be also converted like (1-0.99) MHz=10 kHz. Such a method is known as a heterodyne detection and the well-known technique and well-known element can be also applied and integrated with the pixel 101. The signal of 0 Hz is substantially a detection signal which belongs to a base band and if the object moves dynamically, such a signal has an AC (alternating current) component in accordance with such a motion. Since the ordinary object does not move so fast, by assuring a band width of at most up to a few kHz, it is sufficient. As a base band of an ordinary real-time moving image of about 30 fps or 60 fps, a base band on the order similar thereto is sufficient.

The reason why the frequency (band) of the detection signal from the object is shifted as mentioned above is that there are the following advantages. This is because the typical electromagnetic wave detecting element 111 has a noise in a low frequency area from DC to about 10 kHz and the S/N ratio of the signal from the detecting element 111 is relatively small. An input side noise of the amplifier 112 at the first stage also has a similar tendency. Therefore, it is desirable that the sine wave signal 114 is a signal of 10 kHz or higher. Although a frequency in a high frequency area may be used for the sine wave signal 114, if it is up to about 200 MHz, the sine wave generating unit 102 and the sine wave transmission line 103 can be relatively cheaply constructed. When the number of pixels is relatively large and a physical length of the array in the embodiment is large, an electrical length of the sine wave transmission line 103 is also large. Since a problem such as interference, fading, or the like also occurs, for example, if the length of array is equal to about 30 cm, 100 MHz (which is equal to 3 m as a physical length in the vacuum) or less is typically desirable. Naturally, if a phase difference between the sine waves (signal having the predetermined period) of the pixels is compensated by providing a phase shifter for the transmission line 103 in order to avoid such a problem, the problem can be avoided.

It is a feature of the invention that the transmission line 103 of the signal having the predetermined period is connected to each pixel 101 as illustrated in FIG. 1A for such a reason. In each pixel 101, for an input of the sine wave signal 114, an output of the signal 115 from each pixel becomes the signal of the base band. Therefore, high frequency parts are unnecessary in circuits (for example, switches 110, 108, and 105, wirings 106 and 109, etc.) on the post stage side after that. Since a band width of the signal 115 from each pixel is narrow as mentioned above, a product of the number of pixels and the band width necessary for one pixel can be relatively reduced. Therefore, the modulation frequency can be set to a value lower than that in the related art. For example, if it is intended to assure 30 fps of the real-time moving image at the number of pixels which is equal to 1000×330, the modulation frequency can be set to a low value such as about 9.9 MHz or the like. This is an estimation value on the assumption that the band width of the signal 115 from each pixel is equal to 30 Hz. Finally, it is sufficient that a read-out circuit (not shown) of the detection signal in the x address circuit 107 or the like has a processing ability of the modulation frequency like that, and naturally, such a read-out circuit can be constructed by cheap parts.

Figure 2A:
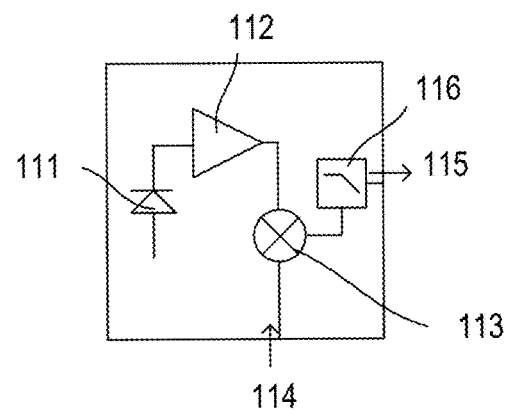
FIGS. 2A, 2B and 2C are diagrams illustrating a construction of a pixel of an image forming apparatus according to a modification of the embodiment 1.
Figure 2B:
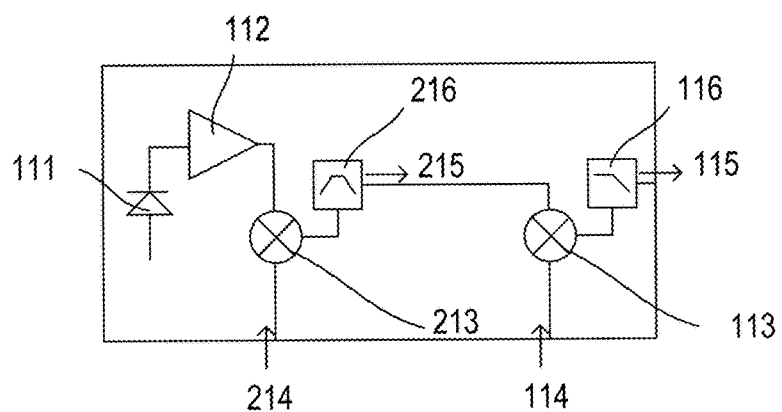
Figure 2C:
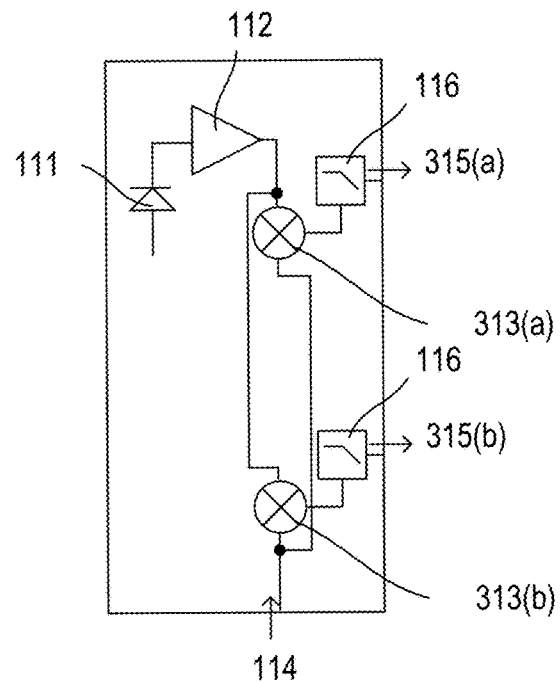

In the embodiment, there are several patterns of the pixel type. FIGS. 2A to 2C are schematic diagrams each illustrating one pixel in the embodiment and are other modifications of FIG. 1B. In FIG. 2A, a low-pass filter 116 to which the frequency-converted signal is input is purposely inserted to the final stage of the demodulated signal and it is an object to eliminate the noise and restrict a spurious band by applying a proper band restriction. The narrower the width is, the higher a noise eliminating ability is. However, an optimum band exists so as not to decrease a frame rate of the moving image. When the sine wave signal 114 in the pixel is synchronized with the modulation frequency of the detection signal from the object, since the synchronous detection is performed, the S/N ratio is relatively large. However, the synchronization is not indispensable.

FIG. 2B illustrates a construction of the pixel of such a super heterodyne type that the signal is not demodulated in a lump but an intermediate frequency signal 215 is temporarily used by using another frequency converter 213. A sine wave signal 214 different from that in FIG. 2A is guided to each pixel. As mentioned above, the pixel is connected to a transmission line for supplying a signal having a predetermined period different from the foregoing signal having the predetermined period and a frequency converting element different from the frequency converting element is further provided for the pixel. In the pixel, the signal is demodulated by two stages. Mainly, such a construction is effective in the case where the modulation frequency is switched at a high speed or is swept. A band-pass filter 216 allows only the signal of about the intermediate frequency to pass, and it is an object to restrict the spurious band and is important.

FIG. 2C illustrates a construction of the pixel of such a direct conversion type that an I-phase signal 315(a) and a Q-phase signal 315(b) are individually demodulated by using π/2 radian phase shifted type frequency converters 313(a) and 313(b). A plurality of π/2 radian phase shifted type frequency converting elements may be provided for the pixel as mentioned above. When comparing with the band-pass filter 216 in FIG. 2B, since the low-pass filter 116 is used for the low frequency area, it can be easily integrated onto a semiconductor substrate and is desirable as an on-chip type image forming apparatus. They are related to the case where the technique which is used in the communication technique is applied to the imaging unit and the well-known technique can be also integrated onto the pixel 101.

Although the embodiment 1 has been described by using the sine wave signal 114, a rectangular wave, a triangular wave, or the like may be used. It is sufficient that the sine wave signal 114 is such a signal 114 that a sine wave signal or a cosine wave signal is contained in its Fourier component (signal 114 having the predetermined period). In other words, it is sufficient that the signal generating unit generates the signal having the predetermined period in which frequencies within a range, for example, from 10 kHz or higher to 200 MHz or lower are contained in the Fourier component.

Embodiment 2

Figure 3:
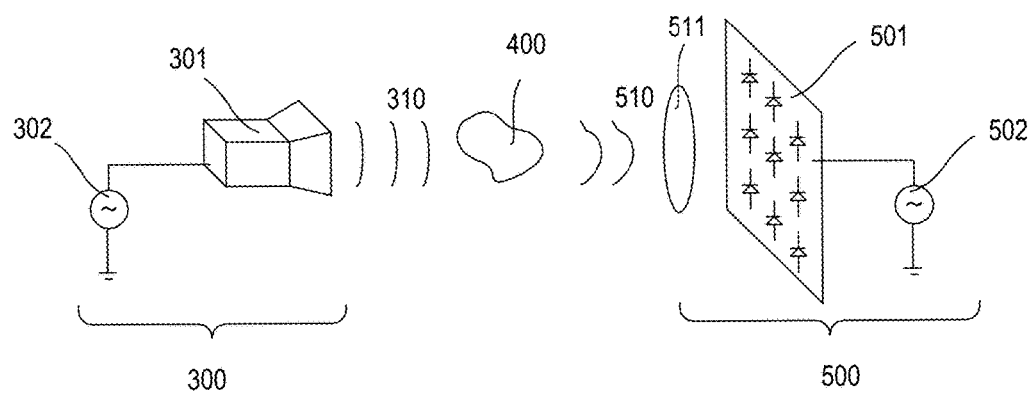
FIG. 3 is a diagram illustrating an imaging system including an array detecting element according to an embodiment 2.

An image forming apparatus according to an embodiment 2 will be described by using FIG. 3. FIG. 3 illustrates an imaging system including the image forming apparatus of the embodiment and an irradiating apparatus for performing an active illumination (irradiating apparatus for performing the active illumination of an electromagnetic wave to the object). In a frequency area from the millimeter wave band to the terahertz band, since an energy of a background black body radiation is small unlike an infrared area, the active illumination is ordinarily used.

In the embodiment, an irradiating apparatus 300 is constructed by a terahertz wave generator 301 and a modulating unit 302. The generator 301 may be an electron device including a negative resistant element such as resonant tunneling diode, Esaki diode, Gunn diode, or the like or an optical device such as quantum cascade laser, p-Ge laser, lead salt laser, or the like. Besides them, the generator 301 may be a continuous light source such as a free electron laser or the like. Or, the generator 301 may be a pulse light source like a light-terahertz wave converting element such as parametric oscillator, photoconductive element, Cerenkov radiation type $LiNbO_3$ generator, or UTC (Uni-travelling-carrier) photodiode. The modulating unit 302 may be any unit so long as it can frequency-modulate or amplitude-modulate their terahertz wave outputs. As mentioned above, the irradiating apparatus includes the modulating unit for modulating the frequency or amplitude of the electromagnetic wave of the active illumination. For example, even in case of the electron device or optical device, it can be directly modulated. Also with respect to the light-terahertz wave converting element which can function as both of the generator 301 and the modulating unit 302, by modulating the excitation light, the frequency modulation and the amplitude modulation can be accomplished.

A terahertz wave 310 which was generated from those generators and was modulated irradiates an object 400. A terahertz wave 510 which had passed through the object or had been reflected therefrom (FIG. 3 relates to an example of a passing construction), includes information of the object 400, and was modulated enters an image forming apparatus 500. At this time, an objective lens 511 may be provided between the image forming apparatus 500 and the object 400. Since a 2-dimensional array detecting element 501 is used in the embodiment, a focal plane array can be constructed. As mentioned above, in the embodiment, the system includes the objective lens arranged between the object and the electromagnetic wave detecting element arranged in a 2-dimensional array form.

The image forming apparatus 500 in the embodiment is constructed mainly by the 2-dimensional array detecting element 501 and a signal generating unit 502 for demodulation. Naturally, a frequency converting unit is built in each pixel in the 2-dimensional array detecting element 501. As a detecting element 501, a Schottky barrier diode or a self-switching diode which can respond to a preferable modulation frequency (10 kHz-100 MHz) is desirable. A rectifier-type detector such as an MIM (Metal-Insulator-Metal) diode or the like or a transistor using a self-mixing of an electron plasma of a channel layer, for example, an FET, HEMT, or the like is also desirable. A QWIP (Quantum-Well-Infrared-Photodetector) using a quantum well or a quantum-type detector using a quantum Hall effect may be used. That is, the electromagnetic wave detecting element is an element selected from the rectifier-type detector, transistor, and quantum-type detector. However, a bolometer which cannot respond to the desirable modulation frequency, a sensor using a pyroelectric effect, a golay cell, or a thermal detector such as a thermo couple is not suitable.

Figure 4A:
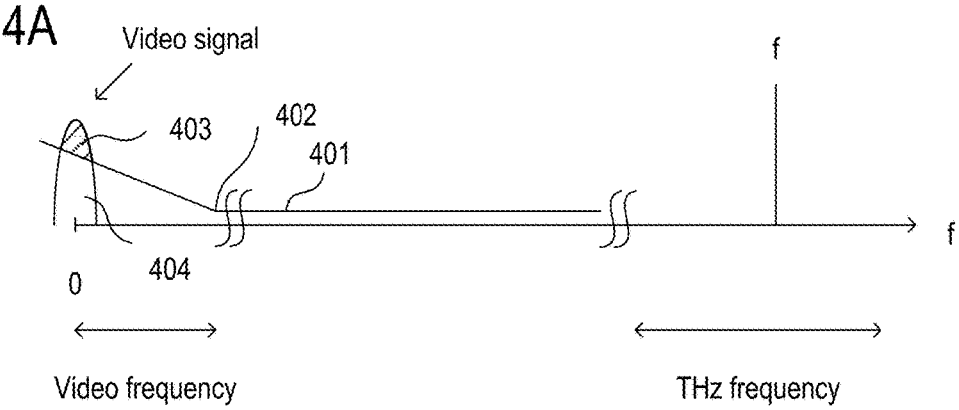
FIGS. 4A, 4B and 4C are diagrams illustrating Fourier spectra of an electromagnetic wave signal from an object according to the embodiment 2.
Figure 4B:
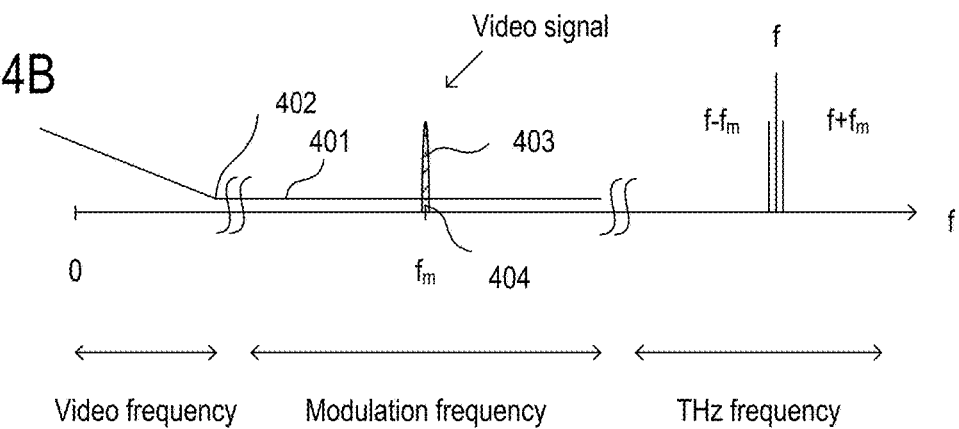
Figure 4C:
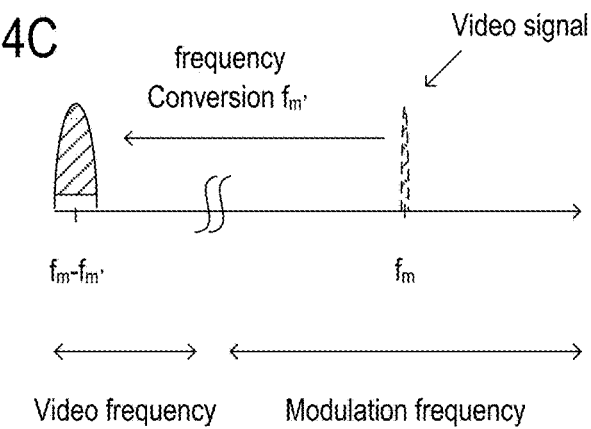

FIGS. 4A to 4C illustrate Fourier spectra of the electromagnetic wave signal from the object showing a comparison between the case where the modulating unit 302 is not used and the case where the modulating unit 302 is used in the imaging system. A frequency on an axis of abscissa indicates a value based on a logarithmic scale. FIG. 4A shows a signal obtained immediately after the detecting element 501 in the case where the modulating unit 302 is not used. A signal of a frequency f in the terahertz band is converted into a DC (direct current) on the basis of a mechanism of the detecting element 501. As such a mechanism, for example, there is a rectification, self-mixing, photon-electronic conversion, or the like. FIG. 4B shows a signal obtained immediately after the detecting element 501 in the case where the modulating unit 302 is used. If the signal is not modulated, a video signal 403 from the object is generated at a frequency near 0 Hz=DC (direct current). Assuming that the modulation frequency is equal to $f_m$, the video signal 403 having a width of about a video band is also generated at a frequency near the frequency $f_m$ in the modulation frequency band. This is because a side band of a differential frequency $f_m$ is generated at a frequency near the frequency f in the terahertz band due to nonlinearity of the detecting element 501. A frequency 402 is a frequency in which a low frequency noise is buried in a white noise and is called a noise corner frequency. Typically, it is located on the high frequency side in the video band. Therefore, since an electric noise 401 of the detecting element 501 which is large on the low frequency side is ordinarily large in the video band, in FIG. 4A, the S/N ratio of the video signal is reduced. Reference numeral 403 indicates S (signal) and 404 denotes N (noise). It will be also understood from the diagrams that the S/N ratio is small at a frequency which is equal to or lower than the noise corner frequency 402. On the contrary, the electric noise 401 of the detecting element 501 which is small on the high frequency side is small in the modulation frequency band and the S/N ratio of the video signal is relatively large in FIG. 4B. However, the video signal 403 near $f_m$ which is difficult to be handled in the case of using such a signal as it is can be frequency-converted to a frequency near DC by mixing a signal frequency $f_{m'}$ from the signal generating unit 502 or the like as shown in FIG. 4C. By this method, the video signal of the excellent S/N ratio can be easily used at a frequency near DC. Naturally, $f_m = f_{m'}$ may be set.

Figure 5:
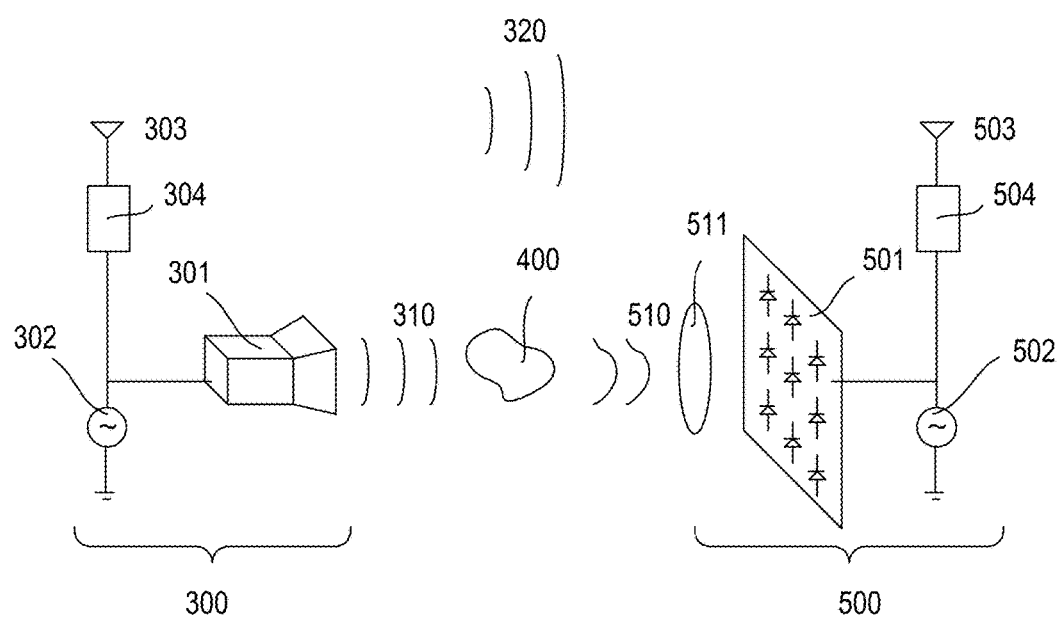
FIG. 5 is a diagram illustrating a construction of an imaging system according to a modification of the embodiment 2.

From such reasons, a frequency difference $f_m - f_{m'}$ is extremely important. Therefore, in the embodiment, the signal generating unit 502 needs to grasp information regarding the modulation frequency held in the modulating unit 302 through some means. For example, if a drift, jitter, or the like occurred in $f_m$, the signal generating unit 502 has to accurately grasp it and feed back to $f_{m'}$. A modification of the embodiment having means for such a purpose is illustrated in FIG. 5. The irradiating apparatus 300 has a management unit 304 of information of the modulation frequency and phase in the modulating unit 302 and can transmit such information by an RF 320 through an RF antenna 303. For example, it is sufficient to use a clock signal. The image forming apparatus 500 receives the information of the modulation frequency and phase in the modulating unit 302 through an RF antenna 503 and controls the frequency and phase of the signal generating unit 502 through a control unit 504. That is, feedback control is made. Naturally, although such control may be made in a wired manner, in the case of a wireless manner, it is more desirable because voluntariness can be provided for a layout of the irradiating apparatus 300 and the image forming apparatus 500.

In the case where there is no need to manage the phase, there is a method whereby it is unnecessary to provide such a communicating unit. For example, by using a rubidium oscillator, a quartz resonator oscillator, or the like having high frequency precision, the modulation frequency $f_m$ in the modulating unit 302 can be precisely managed. Therefore, in this case, the feedback-control of $f_{m'}$ is unnecessary. Even in feed-forward control, it is sufficient. As mentioned above, the irradiating apparatus can have the management unit of the information of the modulation frequency in the modulating unit and the image forming apparatus can have the control unit for controlling the frequency of the signal which is generated by the signal generating unit on the basis of the information of the modulation frequency in the modulating unit. At this time, there is also a case where the irradiating apparatus has the management unit of the information of the phase in the modulating unit and the image forming apparatus has the control unit for controlling the phase of the signal which is generated by the signal generating unit on the basis of the information of the phase in the modulating unit. By using the RF, the control unit can receive the information of at least one of the modulation frequency and the phase which are managed by the management unit.

A further specific image forming apparatus will be described by the following Examples.

Example 1

Figure 6A:
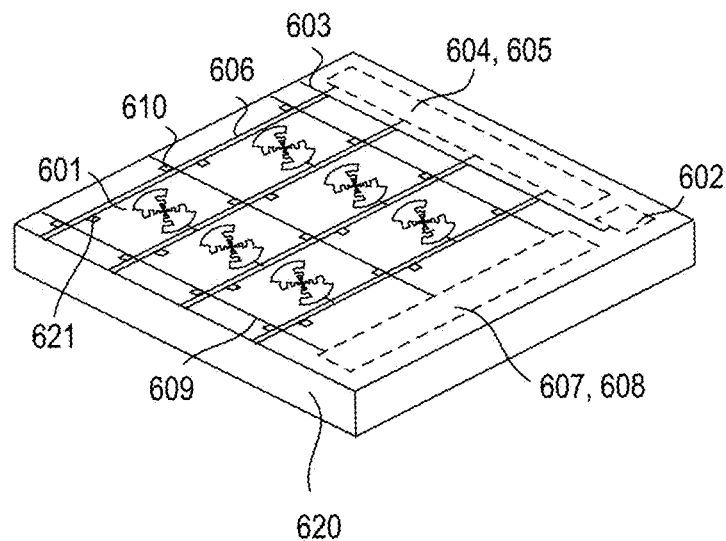
FIGS. 6A, 6B and 6C are diagrams illustrating an array detecting element according to the embodiment 1 and an image forming apparatus using the array detecting element.

More specific Example 1 corresponding to the embodiment 1 will be described. The image forming apparatus according to the Example will be described by using FIGS. 6A to 6C. This Example is an Example including a desirable 2-dimensional array detecting element for imaging the electromagnetic wave in a range from 0.2 THz to 2.5 THz. FIG. 6A is a diagram illustrating a construction of an on-chip type image forming apparatus and FIG. 6B is a diagram illustrating a construction of a pixel.

As for the size of a pixel 601, a short side is equal to 0.6 mm and a long side is equal to 0.8 mm. FIG. 6A illustrates an area of (3×2) pixels as a part of a 2-dimensional array of (200×60) pixels on a chip 620. In this Example, a quartz resonator oscillator integration area 602 is formed on the same chip 620. A quartz is integrated in a CMOS oscillating circuit, thereby oscillating a frequency of 1.4400 MHz. In this case, since a frequency precision on the order of $10^{-6}$ is obtained, it is desirable. A sine wave is supplied from the quartz resonator oscillator integration area 602 to each pixel through a wiring 603. An address circuit integration area 604 and a switch integration area 605 are provided. Any of those areas can be integrated onto the same chip 620 by using a well-known technique. A wiring 606 for read-out is connected between the switch integration area 605 and a pixel switch 610. Similarly, an address circuit integration area 607 and a switch integration area 608 are provided. A wiring 609 for read-out is connected between the switch integration area 608 and the pixel switch 610.

A pixel area in the embodiment is set to 12 cm×4.8 cm and is smaller than an effective wavelength (=80 m) of 1.44 MHz. In the embodiment, a phase shifter 621 is provided for every pixel along the direction of the long array. Each phase shifter 621 progresses the phase by 0.0027 deg. This is because there are only 200 pixels in the direction of the long array and the phase is deviated by about 0.54 deg corresponding to an electrical length in a range from one end pixel to the other end pixel. In the embodiment, a phase shifting circuit using an operational amplifier which can be integrated by a standard CMOS process is integrated. However, in such a relatively small phase difference, an effect of the interference or fading is small and there is no need to provide the phase shifter 621. The phase shifter 621 is effective in the case where the number of pixels is further large or the modulation frequency is relatively large. According to such a design, a frame rate of a moving image which is obtained can be set to a relatively high value such as 120 fps.

Figure 6B:
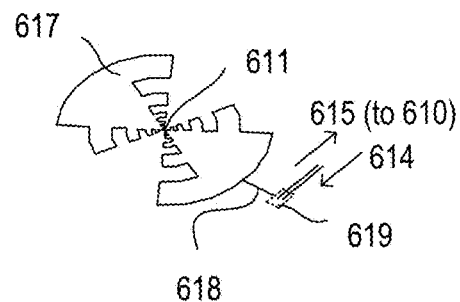

As illustrated in FIG. 6B, the pixel 601 has a Schottky barrier diode 611, a terahertz antenna 617, and a CMOS amplifier • mixer integration area 619. The Schottky barrier diode 611 is attached at a front edge of the antenna 617 and is in contact with a metal serving as an antenna. Although the number of sets of the Schottky barrier diode 611 and the antenna 617 is equal to one for one pixel in the embodiment, two or a plurality of sets may be provided for one pixel. A high impedance line 618 is provided to filter the terahertz wave, can select an electric signal of a frequency of a microwave band or lower, and can send to the CMOS amplifier • mixer integration area 619. Such a structure can be manufactured as follows. For example, a high concentration carrier dope layer and a low concentration carrier dope layer are preliminarily laminated only to a portion near a front edge portion of the antenna 617 in the silicon substrate 620, a metal having a diameter of 0.6 μm is further laminated, and the Schottky barrier diode 611 is provided. After that, an embedding process or the like is performed by using an insulating film and, thereafter, the metal is worked into a predetermined shape so as to form the antenna 617, high impedance line 618, and the like. In the embodiment, a log-periodic antenna is used and is designed into such a shape that a radius up to an outside is equal to 250 μm, a radius up to an innermost side is equal to 10 μm, the number of teeth of a comb of a log-period of 0.7 is equal to 9, and an angle of the tooth of the comb is equal to 45 deg. Such a structure was simulated by a high frequency full electromagnetic field simulator HFSS v. 12 (made by Ansoft Co., Ltd.). Thus, an electromagnetic wave in a wide band from 0.2 THz to 2.5 THz can be detected. The CMOS amplifier • mixer integration area 619 is constructed by a circuit using an operational amplifier or the like and can be manufactured by the standard CMOS process. In the embodiment, it is sufficient that after the CMOS amplifier • mixer integration area 619 was formed onto the silicon substrate 620, the Schottky barrier diode 611 and the antenna 617 are formed in order. When the CMOS amplifier • mixer integration area 619 is worked, the foregoing quartz resonator oscillator integration area 602, address circuit integration areas 604 and 607, and switch integration areas 605 and 608 may be simultaneously formed.

Figure 6C:
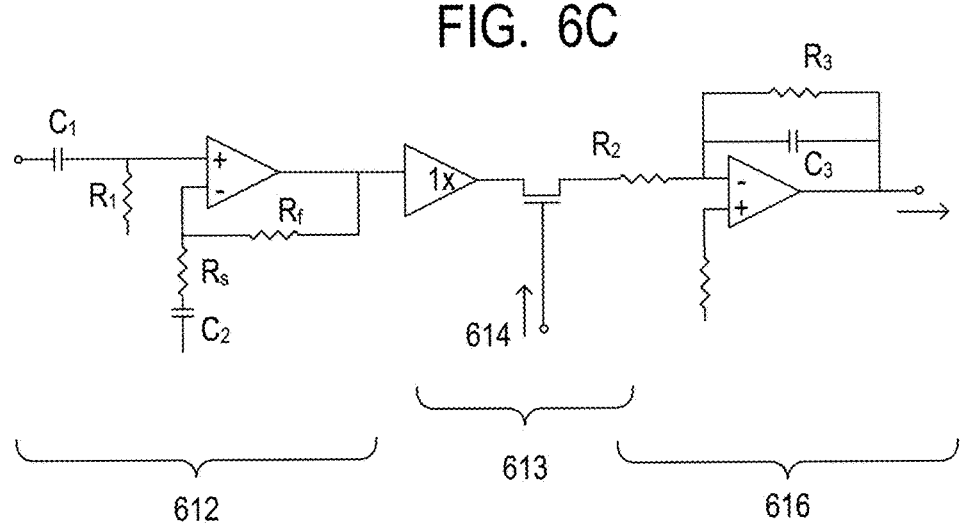

In the embodiment, specifically speaking, the CMOS amplifier • mixer integration area 619 uses a circuit of FIG. 6C. In the diagram, a ground is omitted. An operational amplifier 612 at the first stage is constructed by a non-inverting amplifying circuit for amplifying a voltage signal output of the Schottky barrier diode 611. $C_1$ and $C_2$ are capacitors for AC coupling. $R_f$ and $R_s$ are resistors and decide an amplification degree. $R_1$ is a resistor for reducing an offset that is caused by an input bias current. For example, by using 1 nF, $C_1$ and $C_2$ may be replaced by high-pass filters each for allowing the modulated input signal to pass. When 10 kΩ is selected, $R_1$ can reduce a white noise voltage. As an operational amplifier at the first stage, it is desirable to use such a structure that PMOS transistors of about several stages in which importance is attached to low noise performance rather than a high-speed response are cascade-connected.

An output from such a preamplifier 612 is connected to a mixer unit 613 through a buffer amplifier. Although the simple NMOS type transistor mixer is used in the embodiment, a well-known diode mixer may be used. Any of a single balance type and a double balance type may be used. Since the frequency is equal to about 1 MHz and is low, there is no need to use the rectifying circuit or the like before or after the mixer unit. Since the pixel can be simplified, such a construction is desirable. $R_2$ is a load resistor of the mixer unit 613. The mixer unit 613 mixes a sine wave 614 of 1.44 MHz from the quartz resonator oscillator integration area 602 and the signal obtained through the preamplifier 612, thereby forming a signal containing a demodulated analog signal 615. In the passive mixer 613 in which a gate terminal is an input of the sine wave 614 for demodulation and which does not have the amplifying function of the embodiment, a frequency conversion loss is equal to 1/π. However, if there is no input of the sine wave 614 for demodulation, the apparatus can be also used as an ordinary imaging apparatus instead of the synchronous detection type.

An amplifier 616 at the final stage is constructed by an active low-pass filter and has a function for amplifying the signal 615 obtained after the demodulation and blocking the electric noise and the spurious signal by using $R_3C_3$ which allows, for example, a signal of 120 Hz or lower to pass. It is desirable because a high frame rate of 120 fps in the embodiment can be assured and the noise is also small. It is further better if a higher-order filter is used. The foregoing construction is an example of the CMOS amplifier • mixer integration area 619. A well-known technique can be also used for each of the preamplifier, mixer, and filter. A value of each element may be changed. Naturally, a variable resistor or the like may be used in order to change a frequency of the filter. Although a circuit which can introduce a bias is omitted in the embodiment, a well-known can be also similarly used. Since most of the structure of the embodiment can be integrated by the standard CMOS process, the apparatus is desirable as an image forming apparatus of an on-chip type.

Figure 8:
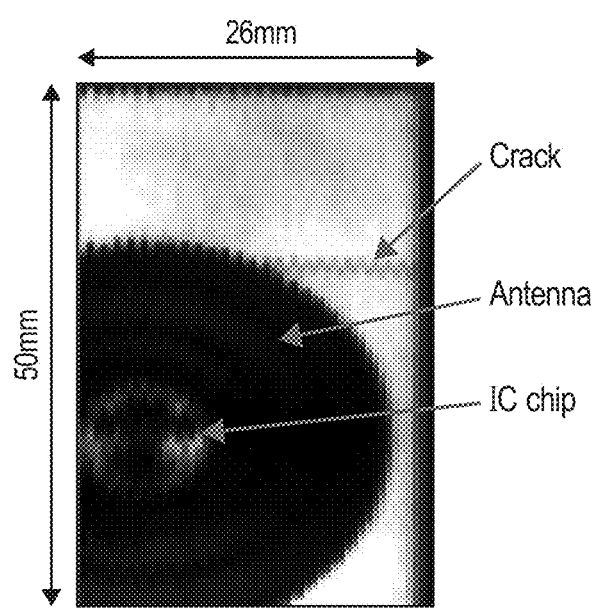
FIG. 8 is a diagram of an imaging example using the image forming apparatus of the embodiment 1 and a terahertz wave irradiating apparatus.

An image pickup example of a fluoroscopic imaging of a frequency of 0.97 THz of an IC chip built-in card using the image forming apparatus of the embodiment and a reverse traveling wave tube oscillator is illustrated in FIG. 8. A terahertz wave from the oscillator is shaped into parallel light by an off-axis parabolic mirror of a diameter=3 inches and F=50.8 mm and is irradiated toward the IC chip built-in card. Further, the terahertz wave which passed through the card is allowed to enter the image forming apparatus of the embodiment by using a resin lens made of cycloolefin of F=127 mm. Since both of a sensitivity of the detecting element of the embodiment and an output of the terahertz wave of the reverse traveling wave tube oscillator are sufficient, the S/N ratio=about 400 in the image of the IC chip built-in card is obtained. Therefore, as shown in FIG. 8, images of the IC chip, the antenna, a crack of plastics of a basic material of the card, and the like can be formed at a high sensitivity. In the reverse traveling wave tube oscillator, although a bias voltage of the reverse traveling wave tube oscillator is directly modulated by a sine wave of 1.4400 MHz by using a commercially available synthesizer, a modulating method of the oscillator is not limited to it. If the modulation is not applied to the reverse traveling wave tube oscillator, it can be also used as an ordinary imaging system instead of the synchronous detection type.

If an electronic shutter technique which is being developed in recent years is used only on the side of the image forming apparatus without applying the modulation to the side of the irradiating apparatus, an image can be similarly formed with a low noise and at a high sensitivity. At this time, if a semiconductor device oscillator such as a resonant tunneling diode or the like which can be driven by a battery is used for the irradiating apparatus, the imaging system can be realized in a compact size.

Example 2

Figure 7A:
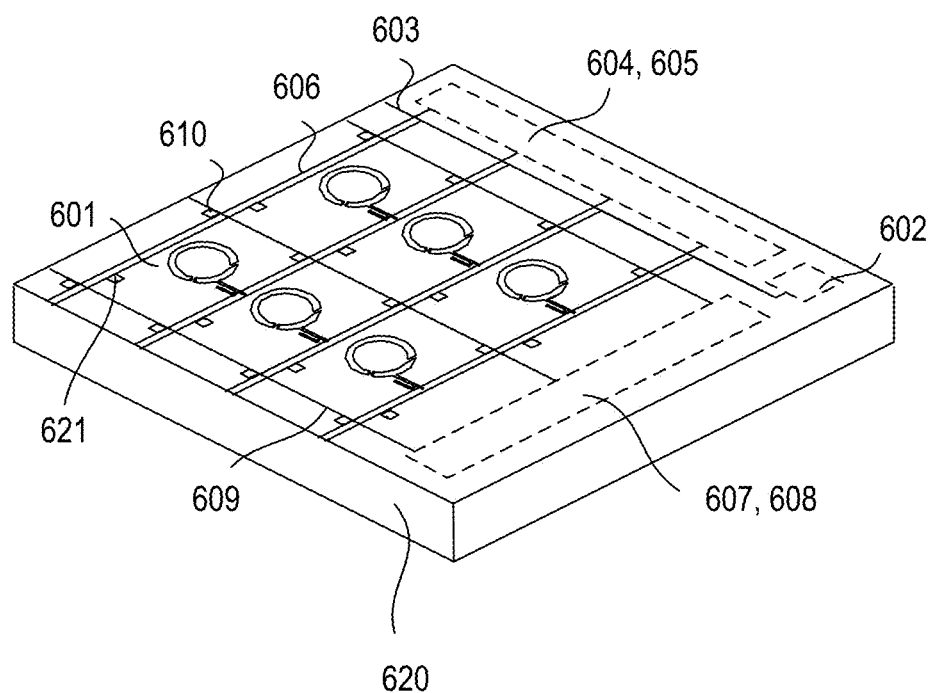
FIGS. 7A and 7B are diagrams illustrating the array detecting element according to the embodiment 2 and an image forming apparatus using the array detecting element.

Example 2 as a modification of the Example 1 will be described. The image forming apparatus according to the Example will be described by using FIGS. 7A and 7B. In this Example, a modification of the antenna 617 is shown. In FIG. 7A, a directional loop antenna of 1.5λ which is perpendicular to the substrate 620 is used. The antenna includes a 2-dimensional array detecting element suitable to image-pickup an electromagnetic wave of about 1 THz.

Figure 7B:
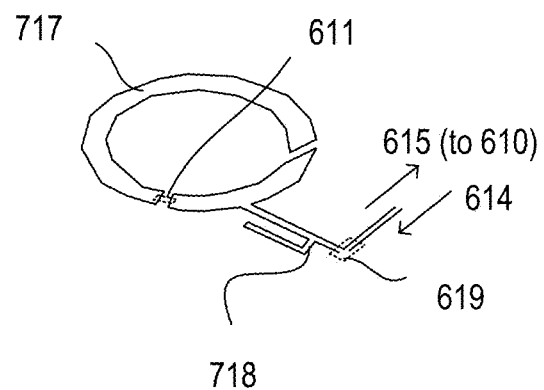

A loop antenna 717 is made of a metal of an inner diameter of 80 μm and an outer diameter of 100 μm. The Schottky barrier diode 611 is connected to a part of the metal portion 717. In FIG. 7B, it is now assumed that a current flows clockwise in the ring antenna 717 and this direction is set to be positive. At this time, nodes of the electromagnetic field exist at positions of 0.25λ, 0.75λ, and 1.25λ in which the electronic element 611 is set to a start point. In the embodiment, the position of 1.25λ is selected and a wiring 718 is designed. An L-type stub is provided and a length is designed to 50 μm (corresponding to 0.25λ) so as to prevent such a situation that the wiring 718 allows the signal to pass and allows the electromagnetic field to leak. If such a wiring 718 with the stub is connected, the electromagnetic field functions without leaking from the antenna 717 to the outside. Such a structure was simulated by the high frequency full electromagnetic field simulator HFSS v. 12. Thus, the following result was obtained. That is, together with a directivity which is perpendicular to the substrate 620, an impedance of about 700 Ω is obtained at a frequency near 0.97~0.98 THz. This is because since it is equal to such a value that the impedance is liable to be matched with the Schottky barrier diode 611 in which the impedance is relatively large and which corresponds to the terahertz wave, the antenna 717 becomes a high efficient antenna. Therefore, it is a desirable example as an antenna 717 which is matched with the Schottky barrier diode 611. Similarly, if an image similar to that of FIG. 8 is obtained, the S/N ratio >1000 is expected and an image can be formed at a further high sensitivity.

According to the embodiment of the invention, the frequency conversion, that is, the demodulating process can be performed in each pixel. The signal to be read out of each pixel has been frequency-converted to the signal of the base band from the modulation signal containing the component of the high modulation frequency. Since a band width of the signal of the base band is equal to the order of the frame rate and is ordinarily narrow, the modulation frequency lower than that in the related art can be selected. In other words, even if the modulation frequency lower than that in the related art is selected, there is no need to reduce the frame rate. Since the signal from each pixel becomes the signal of the base band as mentioned above, high frequency parts are unnecessary in the subsequent circuits. That is, the read-out circuit can be constructed by relatively cheap parts. The image forming apparatus, imaging system, and the like which can perform the image forming and image pickup operations and the like with a low noise and at a high sensitivity by using the desirable nature of the synchronous detection can be provided.

INDUSTRIAL APPLICABILITY

It is expected that the image forming apparatus and imaging system according to the invention are applied as sensors which can be used in manufacturing management, medical image diagnosis, safety management, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-046193, filed Mar. 8, 2013, which is hereby incorporated by reference herein in its entirety.

The invention claimed is:

1. An image forming apparatus configured to form an image by using a terahertz wave, comprising:
   a plurality of pixels, each having an antenna and a Schottky barrier diode connected with the antenna;
   a plurality of switches connected to each of the plurality of pixels;
   a signal generating unit configured to generate a signal having a predetermined period; and
   a transmission line configured to transmit the signal having the predetermined period to each of the plurality of pixels,
   wherein:
   each of the plurality of pixels is further connected to a scanning line for reading out a signal from the corresponding pixel through a corresponding switch among the plurality of switches, and
   each of the plurality of pixels has a frequency converting element configured to convert a frequency of a detection signal of the Schottky barrier diode, using the signal having the predetermined period.

2. The image forming apparatus according to claim 1, wherein the frequency converting element is a mixer.

3. The image forming apparatus according to claim 1, wherein the pixel has a low-pass filter inputting the signal of which frequency is converted.

4. The image forming apparatus according to claim 1, wherein the signal generating unit generates the signal having the predetermined period containing a frequency of 10 kHz-200 MHz as a Fourier component.

5. The image forming apparatus according to claim 1, wherein the transmission line is provided with a phase shifter to compensate a phase difference between signals having the predetermined period of the pixels.

6. The image forming apparatus according to claim 1, wherein the pixel is connected to another transmission line for supplying to the pixel another signal having another predetermined period different from the predetermined period, and
the pixel further has another converting element different from the frequency converting element.

7. The image forming apparatus according to claim 1, wherein the pixel is provided with a plurality of frequency converting elements of π/2 radian phase shifted type.

8. The image forming apparatus according to claim 1, wherein the frequency converting element has a passive mixer.

9. The image forming apparatus according to claim 1, wherein the antenna includes a loop antenna.

10. The image forming apparatus according to claim 9, wherein the loop antenna has two ends, between which the Schottky barrier diode is arranged.

11. The image forming apparatus according to claim 1, wherein the antenna includes a log-periodic antenna.

12. The image forming apparatus according to claim 1, wherein each of the plurality of pixels has an amplifier between the Schottky barrier diode and the frequency converting element.

13. An imaging system comprising:
an irradiating apparatus configured to irradiate an object with an electromagnetic wave; and
an image forming apparatus configured to form an image by using a terahertz wave, the image forming apparatus comprising:
a plurality of pixels, each having an antenna and a Schottky barrier diode connected with the antenna;
a plurality of switches connected to each of the plurality of pixels;
a signal generating unit configured to generate a signal having a predetermined period; and
a transmission line configured to transmit the signal having the predetermined period to each of the plurality of pixels,
wherein:
each of the plurality of pixels is further connected to a scanning line for reading out a signal from the corresponding pixel through a corresponding switch among the plurality of switches, and
each of the plurality of pixels has a frequency converting element configured to convert a frequency of a detection signal of the Schottky barrier diode using the signal having the predetermined period.

14. The imaging system according to claim 13, wherein the irradiating apparatus includes a modulating unit configured to modulate a frequency or an amplitude of the electromagnetic wave.

15. The imaging system according to claim 14, wherein the irradiating apparatus includes a management unit configured to manage information as to the modulation frequency of the modulating unit, and
the image forming apparatus includes a control unit configured to control the frequency of the signal generated by the signal generating unit based on the information as to the modulation frequency of the modulating unit.

16. The imaging system according to claim 15, wherein the irradiating apparatus includes a management unit configured to manage information as to a phase of the modulating unit, and
the image forming apparatus includes a control unit configured to control the phase of the signal generated by the signal generating unit based on the information as to the phase of the modulating unit.

17. The imaging system according to claim 16, wherein the control unit receives through an RF the information as to at least one of the modulation frequency or the phase of the modulating unit.

* * * * *